(12) United States Patent
Cloix

(10) Patent No.: US 8,042,738 B2
(45) Date of Patent: Oct. 25, 2011

(54) METHOD AND SYSTEM FOR TRACKING MEDICAL PRODUCTS

(75) Inventor: Erick Cloix, Camblanes (FR)

(73) Assignee: Implanet, Societe Anonyme (FR)

( * ) Notice: Subject to any disclaimer, the term of this patent is extended or adjusted under 35 U.S.C. 154(b) by 32 days.

(21) Appl. No.: 12/444,735

(22) PCT Filed: Oct. 12, 2007

(86) PCT No.: PCT/FR2007/001675
§ 371 (c)(1),
(2), (4) Date: Apr. 8, 2009

(87) PCT Pub. No.: WO2008/043921
PCT Pub. Date: Apr. 17, 2008

(65) Prior Publication Data
US 2010/0096454 A1  Apr. 22, 2010

(30) Foreign Application Priority Data
Oct. 12, 2006 (FR) ...................... 06 08939

(51) Int. Cl.
*G06F 17/00* (2006.01)
*G06F 7/00* (2006.01)
*G06K 15/00* (2006.01)
*G06Q 30/00* (2006.01)
*G06Q 50/00* (2006.01)
*G06Q 10/00* (2006.01)
*A01K 5/02* (2006.01)

(52) U.S. Cl. .............. 235/385; 235/375; 705/3; 705/28; 705/29; 707/802; 707/803; 340/5.1

(58) Field of Classification Search .................. 235/375, 235/385; 705/3, 28, 29; 707/802, 803; 340/5.1
See application file for complete search history.

(56) References Cited

U.S. PATENT DOCUMENTS
5,969,970 A  10/1999  Rhoades
(Continued)

FOREIGN PATENT DOCUMENTS
DE  19614719 A1  10/1997
(Continued)

OTHER PUBLICATIONS
International Search Report in PCT/FR2007/001675, 3 pages, mailed Jul. 8, 2008.
(Continued)

*Primary Examiner* — Michael G Lee
*Assistant Examiner* — Laura Gudorf
(74) *Attorney, Agent, or Firm* — Banner & Witcoff, Ltd.

(57) ABSTRACT

The present invention concerns a method and a system for tracking medical products in which the product (11, 12) and/or its packaging (16) is marked and identified with a first reference (18) that is stored in a first file (20) and the packaged product is shipped (7) to the client for storage for subsequent use for a patient listed in a second file (31). The references of the product are detected (27) automatically and remotely when it is shipped and stored in a third, or stock control, file (28) of the client at the time of an operation. Removal of the product from stock is detected (30) automatically, the references of the product are inserted in the second file (31) corresponding to the patient of the client for which it is used or is to be used, a fourth file is constructed (36) comprising partial references coming from the file of the patient and the references of the product that have been determined for tracking purposes, and this fourth file is transmitted (52) automatically or semi-automatically to the supplier (4) of the product.

37 Claims, 2 Drawing Sheets

U.S. PATENT DOCUMENTS

| | | |
|---|---|---|
| 7,473,097 B2 | 1/2009 | Raby et al. |
| 2001/0037220 A1* | 11/2001 | Merry et al. ........................ 705/3 |
| 2004/0256469 A1* | 12/2004 | Faenza et al. ................. 235/492 |
| 2005/0010448 A1* | 1/2005 | Mattera ............................. 705/3 |
| 2006/0089888 A1* | 4/2006 | Roger ............................. 705/28 |
| 2006/0138221 A1 | 6/2006 | Swan et al. |
| 2006/0232408 A1 | 10/2006 | Nycz et al. |
| 2007/0299421 A1* | 12/2007 | Gibson ........................ 604/506 |

FOREIGN PATENT DOCUMENTS

| | | |
|---|---|---|
| FR | 2776790 A1 | 10/1999 |
| FR | 2865193 A | 7/2005 |
| FR | 2878053 A | 5/2006 |
| WO | 9639099 A | 12/1996 |
| WO | 9966444 A | 12/1999 |
| WO | 0135872 A | 5/2001 |
| WO | 2004008387 A | 1/2004 |
| WO | 2004008387 A1 | 1/2004 |
| WO | 2008043921 A2 | 4/2008 |

OTHER PUBLICATIONS

WO 2005/019969 A2; dated Mar. 3, 2005.

International Search Report FR Application No. 10/00659 dated Sep. 15, 2010.

Article—Henning Baars Et al: "Combining RFID Technology and Business Intelligence for Supply Chain A Optimization Scenarios for Retail Logistics" Hawaii International Conference on System Sciences, Proceedings of the 41st Annual IEEE, Piscataway, NJ, USA, Jan. 1, 2008, p. 73.

* cited by examiner

METHOD AND SYSTEM FOR TRACKING MEDICAL PRODUCTS

This application is a U.S. national stage of PCT/FR2007/001675, filed on Oct. 12, 2007, which claims priority to French application no. 0608939 filed on Oct. 12, 2006.

The present invention concerns a method and a system for interactive and continuous tracking of medical products, enabling total traceability thereof, notably for insurance and after-sales service purposes, whilst guaranteeing that medical confidentiality is preserved.

It finds a particularly important, although not exclusive, application in the field of internal prostheses, such as those of the knee, hip, etc., which are liable to wear and/or to change over time, leading to the necessity for a replacement or for further surgery.

It is notably of particular benefit when using innovative surgical implants or implants that have become the norm or generic.

By minimizing costs, it contributes to the savings that have become imperative by virtue of the evolving market linked to ageing of the population and the necessity for ever greater medical cover.

It also finds an important application in the field of tracking medications, notably by providing virtually instantaneous access to products that represent a risk, have been sold to individual persons and suddenly need to be withdrawn and/or recalled.

Methods and devices are already known for storing information to enable automatic restocking of products that have been sold, based on entry and exit of products to and from a warehouse. Such systems (which generally use barcodes) cannot track products beyond the warehouse, in particular in the home of the actual end user.

Systems for overall management of data concerning a patient are also known, in particular for tracking patients in hospital.

Such systems do not take account of the intervention of external services not bound by professional confidentiality and employing more ordinary industrial practices.

Also known (WO 2004/008387) is a system for monitoring medications or prescriptions using microchips or labels transmitting and receiving radio frequencies.

In particular, such systems cannot track information reliably and unambiguously.

The invention aims to provide a method and a system for tracking medical products, such as surgical implants in particular, which method and system represent a better response to practical requirements than previously, notably by providing traceability and reliable and uninterrupted tracking of products, from the manufacturer to the patient, with automated and considerably simplified logistics. The product is intended to be used by and/or implanted in a named patient, whose medical confidentiality is nevertheless preserved, in compliance with statutory standards in respect of traceability that until now have not been complied with, in the absence of satisfactory methods for their implementation, at the same time as minimizing costs.

The invention now enables professionals to comply with a legal requirement whose implementation has been attempted for many years without success.

Moreover, using the invention, not much manual intervention is required of the hospital, paramedical and/or medical staff, which improves safety by minimizing the risk of human error, at the same time as, if necessary, providing a filter to ensure that medical confidentiality is preserved.

Immediate identification of patients affected by a problem or potential problem in respect of a type of implant or medication also becomes possible, which is a considerable advantage, with the potential for saving human lives.

The invention also greatly facilitates management for medical bodies such as hospitals, pharmacies or doctor's surgeries, for suppliers of medications and/or implants, and for doctors, thanks to permanent and immediate access to some or all of the databases concerning the products concerned via any kind of data sorting or analysis means.

With this aim, the invention essentially proposes a method of tracking medical products in which the product and/or its packaging is marked and identified by the supplier of the product with a first reference that is stored in a first file and the packaged product is shipped to a client for storage by the client for subsequent use by or implantation in a patient listed in a second file, characterized in that the references of the product are detected automatically and remotely when it is shipped and stored in a third, or stock control, file of the client, the removal of the product from stock is detected automatically, the references of the product are inserted in the second file corresponding to the patient of the client for which it is used or is to be used, a fourth file is constructed comprising partial references coming from the file of the patient and the references of the product that have been determined for tracking purposes, and this fourth file is transmitted automatically or semi-automatically to the supplier of the product.

Advantageous embodiments use one or more of the following features:

- the medical product is a surgical implant;
- the medical product is a medication;
- the simultaneous or substantially simultaneous removal from stock of the references of at least two products is detected automatically and the references of the product used for the patient are inserted automatically in the second file by automatic detection and then subtraction of the product or products re-entered into stock after the operation, with the products removed;
- the products and/or their packaging are marked and detected by optical recognition means;
- the products and/or their packaging are marked and detected by radio-frequency recognition means;
- the product corresponding to the fourth file is re-ordered automatically for the client concerned;
- an Intranet or Internet computer network is used to interrogate and to dialogue with the remote data storage server of the supplier to order and transmit the fourth file and update the first file of products, if necessary;
- the various files are sorted and analysed to identify and mark automatically or semi-automatically products and/or patients affected by a potential or existing problem linked to said product and/or to the type of patient.

The invention also proposes a system implementing the method as described above.

It also proposes a system for tracking medical products comprising means for marking and identification of products and/or their packaging with a first reference, means for storage of said references in a first file, means for storage following transport of at least one of the packaged products by a client with a view to subsequent use thereof for a patient listed in a second file of said client, characterized in that it further includes means for automatic and remote detection of the references of the product when it is shipped, means for storing said references in a third, or stock control, file of the client, means for automatic detection of removal and/or entry of one or more products from/into said stock, means for insertion of the references of the product into the second file corresponding to the patient of the client in which it is or will be implanted, means for forming a fourth file comprising partial references coming from the file of the patient and the references determined of the product used, for tracking purposes, and means for automatic or semi-automatic remote transmission of this fourth file to the supplier of the product.

It advantageously includes means for marking and detecting products and/or their packaging by optical recognition.

The product being placed in packaging comprising a transparent face or a transparent box, it is equally advantageous if the marking means are glued or stuck to the inside of said transparent face of the packaging containing the product.

Although such a label is more difficult to apply, it has the particular advantage of improved protection.

One advantageous embodiment includes means for marking and detection of the products and/or their packaging by radio-frequency recognition.

An RFId (Radio Frequency Identification) label is advantageously used for this purpose, notably fixed to the interior of the packaging.

For example, a surface carrying no information (internal face of the packaging and/or of a flap of the packaging) is used, which enables the selection for each size of box of the maximum size RFId chip so that reading of the chip is optimized (transmit-receive distance).

This also improves protection of the RFId microchip against damage caused by manipulation during handling, transportation and storage.

This avoids coexistence with the external labelling of the box, which would make it obligatory to reduce the size of the RFId microchip (or that of the labelling), to the detriment of optical and radio legibility, or to choose an RFId microchip serving also as a label (paper face carrying legally required information such as: designation, size, reference, etc.).

In another advantageous embodiment, the label is stuck on so that its bottom right-hand corner is as close as possible to the bottom right-hand corner of the packaging and/or its flap.

Such positioning of the RFId chip optimizes its detection and reading by any portable radio wave transmission-reception means. It has been observed that hospital personnel have a natural tendency to align the reading means with the right-hand side of boxes.

Another advantageous embodiment includes means adapted to re-order automatically the product corresponding to the fourth file for the client concerned.

Equally advantageously, it includes means adapted to use an Intranet or Internet computer network to interrogate and dialogue with the remote data storage server of the supplier to order and to transmit the fourth file and update the first file of products, if necessary.

Even more advantageously, it includes means for sorting and analysing the various files to identify and mark automatically or semi-automatically products and/or patients affected by a potential or existing problem linked to said products and/or to the type of patient.

In one advantageous embodiment, the product marking and identification means also comprise at least one card attached to an RFId label contained in the product packaging.

This credit card format card initially contains no identifier and the RFId microchip that is integrated into it contains only information for the product contained in the packaging.

Following the operation, the card contains the partial identity of the patient and the date and type of operation carried out.

It then receives, via radio, all the data concerning the implant used (designation, reference code, batch number) stored in the RFId microchip. The card can then be returned to the patient.

Accordingly, during post-operative follow-up consultations, it can be used to store additional information on post-operative action.

During consultations with a view to potential further surgery, it enables immediate recovery of all the patient/product information, simply by reading the microchip.

It also has an individual serial number, and in the event of planning further surgery in the same hospital, this enables automatic recovery of all the data for the previous operation, either directly by reading a file contained in the microchip or by automatically calling up the patient file.

In one embodiment, the individual serial number of the card provides access to the partial file of the patient via the Internet site of the manufacturer of the device. This function is used if the hospital in which the consultation takes place is not (or no longer) equipped with the system.

The patient card can advantageously be further equipped with a detachable portion (electronic microchip) that can be inserted into a memory card reader to consult patient information.

The partial files referred to hereinabove are advantageously created automatically when information from the RFId microchip of the implant is entered into the patient file that is the property of the hospital.

The partial files, which enable the manufacturer to obtain a great quantity of information from which personal information relating to the patient is excluded, therefore provide absolute protection of medical confidentiality.

What is more, the partial files of the various implants can be cross-referenced so that it is possible to tell the precise number of implants of each category that have been implanted, with their actual implantation dates, and the pathologies for which they were used.

This data can also be used to draw up automatically implant survival curves and therefore to obtain an ongoing overview of the real service life of each type of implant.

Finally, the patient card described above is useful for tracking the company's implants as it can decrement the number of implants each time that a revision (withdrawal of a prosthesis) is effected.

This constitutes an exceptional result because, unless extremely costly studies are carried out, no implant manufacturer is at present capable of this level of traceability in the context of medical devices vigilance at the same time as preserving medical confidentiality.

The advantage of this use of partial files and patient cards for the post-market tracking required by international quality standards is also clear.

Thus although the company cannot tell the identity of patients, an immediate match can be established by the hospital between the partial files contained in the information system of the company and the patient files contained in its own database.

This makes it possible to identify almost instantaneously the patients to be contacted in the context of medical devices vigilance (product recall).

The invention will be better understood on reading the following description of embodiments provided by way of nonlimiting example. The description refers to the accompanying drawings, in which:

FIG. 1 is a diagram 1 showing the principle of the method of the invention.

Figure 1:
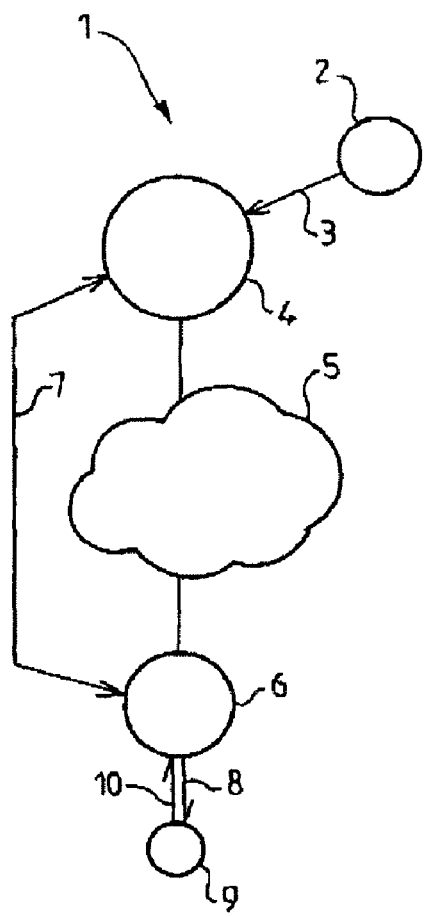
FIG. 1 is a general diagram showing the principle of the method of the invention.

Products manufactured by an industrial company 2 are shipped (arrow 3) to the product supplier 4, where they are packaged and marked with a first reference stored in a first file.

The products are then ordered by the client 6 (a hospital, a pharmacy, a doctor, etc.) via the Internet 5, by telephone, or by any other means, and then shipped (arrow 7). On arrival, they are detected automatically and their references are stored in a third file.

At the time of use, they are removed from stock (arrow 8) and transmitted for use at 9, where they are detected automatically.

The chosen product is then taken by or implanted in the patient, the products not used being returned to stock (arrow 10) and detected again.

Information corresponding to patients and implants is taken into account to form the fourth file, which is then forwarded via the Internet 5 for tracking the product as necessary to comply with statutory provisions, etc., and/or for re-ordering by the supplier 4.

Hereinafter, the same numbers will be used to identify the same references or identical or similar references.

Figure 2:
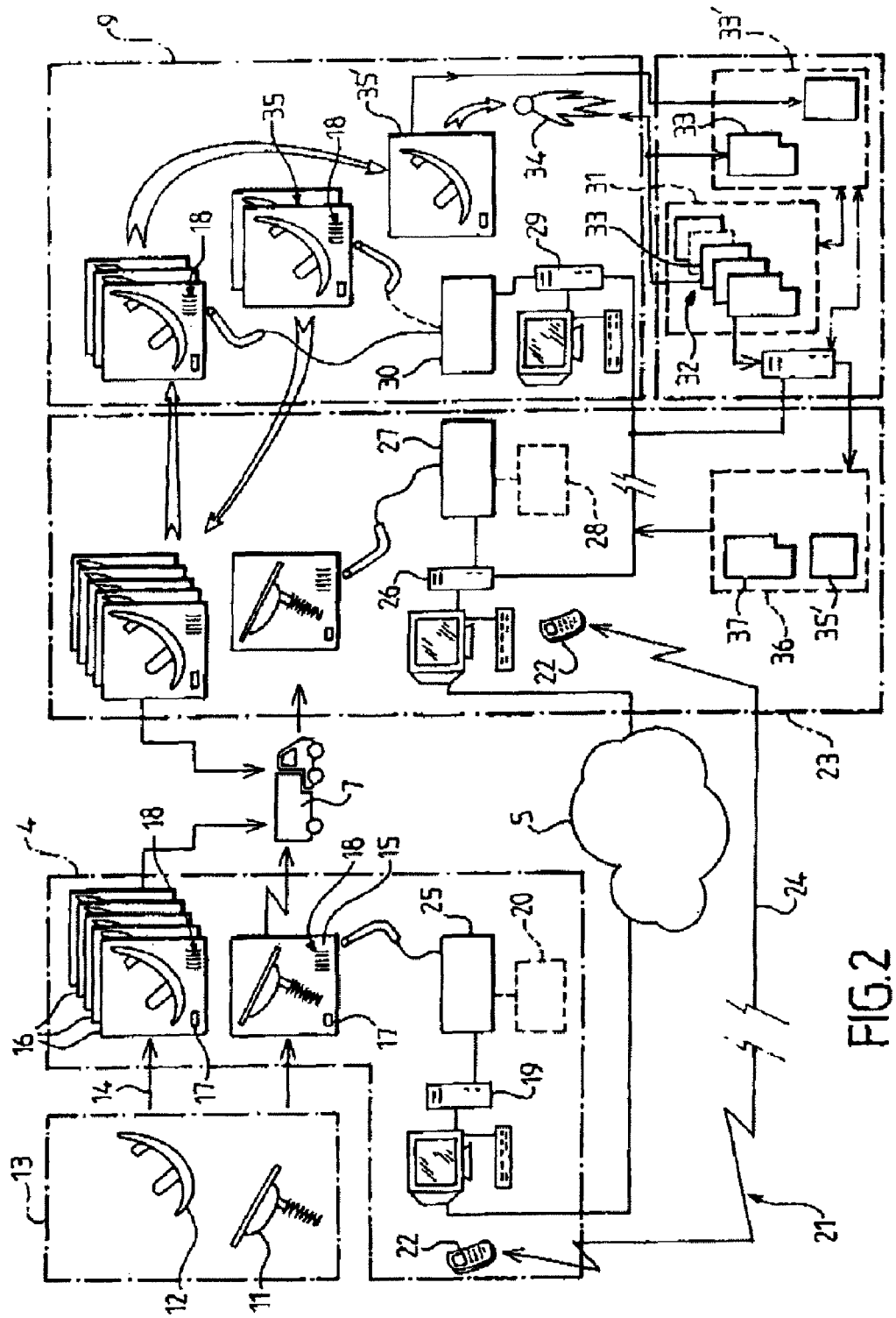
FIG. 2 shows diagrammatically a system and its operation in the embodiment of the invention more particularly described here, applied to surgical implants.

FIG. 2 shows in more detail the embodiment of the invention more particularly described here.

Implants 11, 12 manufactured by a first manufacturer 13 are ordered by the supplier 4 (arrow 14), who packages the implants, for example by placing them in sachets 15, 16.

These sachets are here marked by numbers 17, colour codes, microchips (not shown) and/or barcodes 18 in a manner that is known in itself, to form first references establishing a one-to-one relationship between an identifier and an implant. The references of the implants and/or their sealed packaging are then entered into a computer 19 to constitute a file 20 designated "FILE N° 1" of implants available from and listed by the supplier.

| "FILE N°1" | | | |
|---|---|---|---|
| PRODUCT NAME | Format | Width | Example |
| Denomination | Alpha | 20 | Right internal condyle |
| Product family | Alpha | 8 | TARTAR |
| Type | Alpha | 10 | P0950D01 |
| Kind | 999 | 3 | —* |
| Size | 99 | 2 | 45* |
| Materials | Alpha | 10 | Titanium |
| PRODUCT REFERENCE | | | |
| Manufacturer | 999 | 3 | —* |
| Supplier | 999 | 3 | —* |

| "FILE N°1" (continued) | | | |
|---|---|---|---|
| PRODUCT NAME | Format | Width | Example |
| Batch number | Alpha Num | 8 | 02P114 |
| Size | Alpha Num | 3 | H08 |
| STERILIZATION | | | |
| Sterilization method | 99 | 2 | — |
| Sterilization expiry | yy mm | 4 | 06 07 |
| Sterilization batch | 99 | 2 | —* |

*Supplier internal code

A surgery clinic 23 places an order (arrow 24) via the Internet 5 and/or other means 21, such as by telephone 22; the order is entered into the computer 19, which comprises calculation, analysis, printing, etc. means for data corresponding to the order and to the types of implants ordered.

This order authorizes the removal from stock of the implants, which are automatically logged by reading their bar code (device 25) or by other means (not shown), such as remote reading of a microchip integrated into the packaging and/or the implant.

The data concerning implants ordered and removed from stock for shipping are also transmitted for confirmation purposes to the computer 26 of the clinic 23 via the Internet, for example.

The products ordered are then shipped to the clinic (delivery van 7).

On arrival, they are detected automatically and remotely by means 27 located on the client premises to constitute a file 28 designated "FILE N° 3", for example of the following type.

| "FILE N°3" | | | |
|---|---|---|---|
| STORAGE ESTABLISHMENT | Format | Width | Example |
| Department | | | |
| Pharmacy | Alpha Num | 8 | Block 2 |
| Surgical department | Alpha | 15 | Orthopaedics |
| Operating theatre | Alpha Num | 8 | Theatre3 |
| Date | | | |
| Creation of form | dd mm yy | 6 | 15 01 06 |
| Movements | 99 | 2 | 03 |
| Last movement | dd mm yy | 6 | —** |
| Product name | | | |
| Designation | Alpha | 20 | Right internal condyle |
| Product family | Alpha | 8 | TARTAR |
| Type | Alpha Num | 10 | P0950D01 |
| Kind | 999 | 3 | —* |
| Size | 99 | 2 | 45* |
| Materials | Alpha | 10 | Titanium |
| Product reference | | | |
| Manufacturer | 999 | 3 | —* |
| Supplier | 999 | 3 | —* |
| Batch number | Alpha Num | 3 | 02P114 |
| Size | Alpha Num | 3 | H08 |
| Sterilization | | | |
| Sterilization method | 99 | 2 | —* |
| Sterilization expiry | yy mm | 4 | 06 07 |
| Sterilization batch | 99 | 2 | —* |

*Supplier internal code
**Hospital internal code

If a surgeon is to operate in operating theatre 9, similar means programmed accordingly, for example a computer or a PDA 29 and a bar code and/or microchip card reader 30, detect the references 18 of the implants necessary a priori.

There are generally several implants of different sizes, the size to be used often being chosen by the surgeon at the last moment.

At the same time, and from the file 31 designated "FILE N° 2" containing the medical records 32 of the patients of the department, the medical record 33 of the patient 34 to be operated on is obtained from the computer 29, for example.

"FILE N°2"

| PATIENT NAME | Format | Width | Example |
|---|---|---|---|
| Name | Alpha | 20 | — |
| Forename | Alpha | 20 | — |
| Date of birth | dd mm yy | 6 | — |
| Place of birth | Alpha | 10 | — |
| Social security number | 9999999999 | 10 | — |
| Address | Alpha Num | 20 | — |
| Telephone | 9999999999 | 10 | — |
| E-mail | Alpha | 40 | — |
| Previous surgery | Alpha | 40 | Appendicitis |
| Risk factors | Alpha | 30 | Haemophilia |
| SURGERY | | | |
| Establishment | Alpha Num | 40 | NECKER |
| Department | Alpha Num | 15 | Orthopaedics |
| Surgeon | Alpha | 20 | — |
| Type of surgery | 999 | 3 | —** |
| Location of surgery | Alpha | 20 | Right knee |

**Hospital internal code

The surgeon operates and then returns the unused implants 35, which are automatically and remotely detected by the device 30, the difference giving the references of the implant 35' that has been used.

The bar code or the identifier of the latter implant can also be read directly rather than obtained from the difference.

A hybrid record 33' is then assembled and used on the one hand to update the file 33 of the patient (whose medical history from now on includes the operation) and to produce the record 36 designated "FILE N° 4" containing partial references 37 enabling the medical confidentiality of the patient operated on to be preserved and the references of the implant 35' that have been determined.

"FILE N°4"

| PATIENT | Format | Width | Example |
|---|---|---|---|
| Name | Alpha | 20 | — |
| Forename | Alpha | 20 | — |
| Date of birth | dd mm yy | 6 | — |
| Place of birth | Alpha | 10 | — |
| Social security number | 9999999999 | 10 | — |
| Address | Alpha Num | 20 | — |
| Telephone | 9999999999 | 10 | — |
| E-mail | Alpha | 40 | — |

-continued

"FILE N°4"

| PATIENT | Format | Width | Example |
|---|---|---|---|
| SURGERY | | | |
| Establishment | Alpha Num | 40 | NECKER |
| Department | Alpha Num | 15 | Orthopaedics |
| Surgeon | Alpha | 20 | — |
| Type of surgery | | | |
| Description | Alpha | 30 | — |
| DRG | | | —** |
| Location of surgery | Alpha | 20 | — |
| Limb | Alpha | 20 | Leg |
| Joint | Alpha | 20 | Knee |
| Right/left | Alpha | 1 | R |
| Implant fitted | 999 | 3 | —** |
| RAS | 999 | 3 | —** |
| Problems | 9 | 1 | 5** |

**Hospital code

The fourth file is then transmitted automatically or semi-automatically, for example on validation by medical staff pressing a key, via the networked computer 26, to the supplier 4 via the Internet 5.

The information received is then processed (19) by data processing means to track the implant in accordance with legal requirements and for other operations such as re-ordering, for example.

Figure 3:
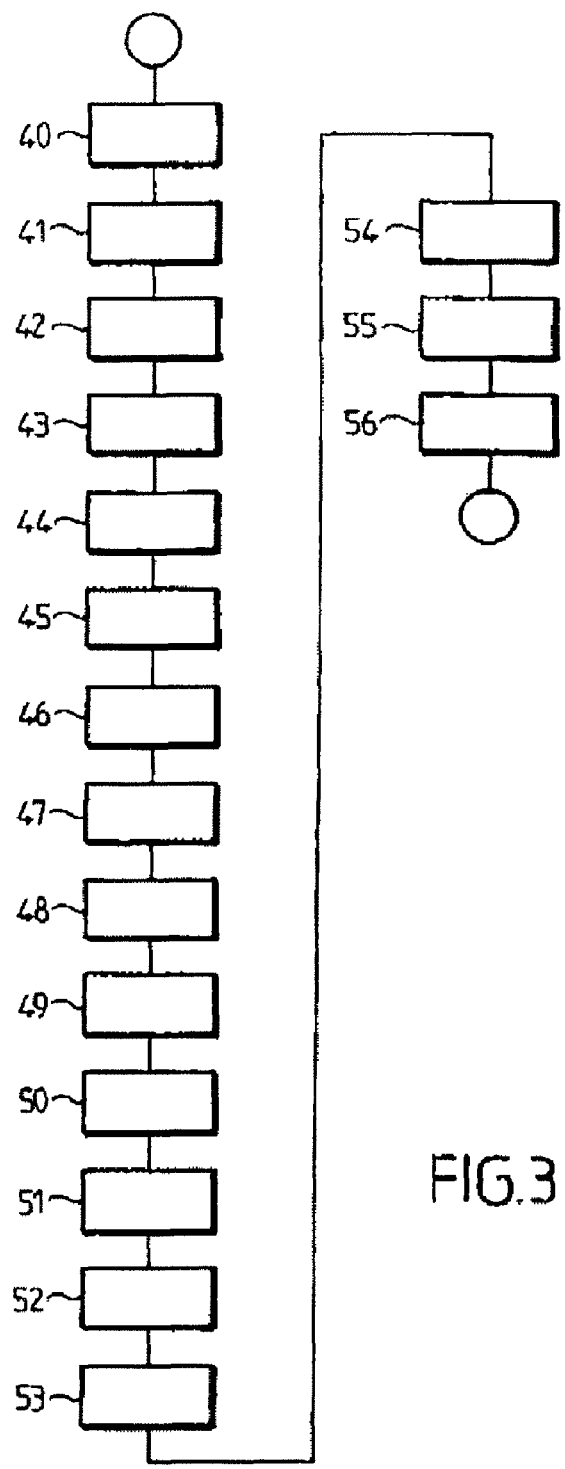
FIG. 3 is a block diagram showing the sequence of steps executed in the method of the invention more particularly described here.

The operations of the invention in the embodiment more particularly described here with reference to the FIG. 3 functional flowchart are described and represented hereinafter.

After manufacture 40 by the manufacturer of the implants concerned, there follows a step 41 of ordering by the supplier. The product having been shipped, it is then stored by the supplier (step 42) who identifies and marks it in a manner known in itself (step 43).

At the same time, the supplier constructs FILE N° 1, as described above.

There follows a step 44 of ordering by the hospital 46, followed by shipping (step 45). On completion of shipping, FILE N° 3 is constructed by remote scanning and storage (step 46) of implants introduced into the hospital stores, for example by a bar code reader and/or a contactless microchip card reader.

On use of an implant following a request from a surgeon, a step 47 of removing the implants necessary for the operation from the hospital stores is effected with automatic detection 48 of said implants by identical means.

In step 49 the operation is effected by the surgeon (the medical records of the patient concerned are obtained beforehand from the hospital FILE N° 2).

After the operation has been carried out, the implants that have not been used are returned to the hospital stores and are detected automatically (50).

There follows a step 51 of constructing FILE N° 4, expurgated to protect the medical confidentiality of the patient operated on.

In other words, FILE N° 4 therefore contains non-confidential information on the patient and information on the implant that has been implanted in the patient.

A step 52 of transmitting the elements of FILE N° 4 to the supplier enables complete tracking of the implant via the operation on the patient.

A step 53 of verification and storage of the files is followed by updating of the implants file (FILE N° 1) by the supplier (step 54), possibly followed by a step 55 for automatic re-ordering of new implants as a function of that to be used in the operation, and possibly a final step 56 of producing and analysing statistics linked to the implants and/or to the types of operation linked to a particular type of patient.

It goes without saying, and also follows from the foregoing description, that the present invention is not limited to the embodiments more particularly described. To the contrary, it encompasses all variants and in particular those in which the product is a medication or a series of medications intended for complex and/or vital treatments, such as treatment for AIDS, for example, or for degenerative neural diseases such as Alzheimer's or Parkinson's disease.

The invention claimed is:

1. A method of tracking medical products in which a marked packaged medical product is identified by a supplier of said product by a first reference stored in a first product file, the medical product being stored at a client facility for subsequent use for a patient identified in a second patient file, the method comprising the steps of:
   detecting the first reference of the medical product automatically and storing said first reference in a third client file,
   detecting removal of the product from stock automatically,
   inserting the first reference of the removed medical product in the second patient file corresponding to a patient for which the medical product is used or to be used,
   constructing a fourth file comprising partial references coming from the second patient file, said fourth file comprising the first reference of the medical product and expurgated patient data which includes a patient identifier but protects the medical confidentiality of the patient, and
   transmitting the fourth file automatically or semi-automatically to the supplier of the product.

2. A method of tracking medical products in which a marked packaged medical product is identified by a supplier of said product by a first reference stored in a first product file, the medical product being stored at a client facility for a subsequent use for a patient identified in a second patient file, the method comprising the steps of:
   (1) receiving from a third client file the first reference of the medical product previously detected automatically and stored in said third client file,
   (2) inserting the first reference of the medical product of which removal from stock has been detected automatically in the second patient file corresponding to a patient for which the medical product is used or to be used,
   (3) constructing a fourth file comprising the first reference of the medical product and partial references coming from the second patient file, said partial references being expurgated information which includes a patient identifier but protects the medical confidentiality of the patient, and
   (4) transmitting the fourth file automatically or semi-automatically to the supplier of the product.

3. A method according to claim 2, wherein said marked packaged medical product comprises a removable packaging and a detachable card attached to an RFID microchip contained in said removable packaging, and wherein said RFID microchip comprises a RFID memory file loaded with information on said medical product contained in said packaging, said method further comprises the steps of,
   storing in said RFID memory file information on the patient and on the date and type of operation carried out in said microchip, and
   further using said card for storing additional information on post-operative action.

4. A method of tracking medical products in which marked packaged medical products are identified by at least a supplier of said medical products with corresponding first references stored in first product files, the medical products being stored at a client's facilities for subsequent use for corresponding patients identified in second patient files, wherein each of said marked packaged medical products comprises a removable packaging, a card attached to an RFID microchip contained in each of said packaging, wherein each of said RFID microchips comprises a RFID memory file containing information on respective products and partial references coming from one of the second files of a patient operated on with a respective medical product, said method comprising the step of cross-referencing RFID memory files of several microchips to determine the number of medical products used in operations, actual implantation and pathologies for which the products are used, wherein said partial references on said RFID memory files contain expurgated information which includes a patient identifier but protects the medical confidentiality of the patient.

5. The method according to claim 4, further comprising sorting and analyzing said RFID memory files to identify and mark automatically or semi-automatically products or patients affected by a potential or existing problem limited to said products or to a type of patient.

6. The method according to claim 1, wherein the medical product is a surgical implant.

7. The method according to claim 1, wherein the medical product is a medication.

8. The method according to claim 1, further comprising:
   automatically detecting a simultaneous or substantially simultaneous removal from stock of at least two medical products and automatically inserting references of the two medical products used for the patient in the second patient file and then removing medical products re-entered into stock after operation on the patient.

9. The method according to claim 1, wherein the marked packaged medical product has removable packaging that is configured to be marked and detected by optical recognition means.

10. The method according to claim 1, wherein the marked packaged medical product has removable packaging that is configured to be marked and detected by radio-frequency recognition means.

11. The method according to claim 1, wherein said marked packaged medical product comprises removable packaging and a detachable card attached to an RFID microchip contained in said packaging, wherein said RFID microchip is loaded with information on said medical product contained in said packaging, information on the patient, date and type of operation carried out are stored in said RFID microchip, and further comprising the step of using said card for storing additional information on post operative action.

12. The method according to claim 11, wherein said RFID microchip has an individual serial number enabling automatic recovery of all the data for any previous operation, either directly by reading a file contained in the microchip or by automatic calling up of the patient file.

13. The method according to claim 11, wherein the card is further equipped with a detachable portion arranged to be inserted into a memory card reader, further comprising the step of inserting said detachable portion in said reader to consult patient information.

14. The method according to claim 11, wherein the fourth file is automatically created when information from the microchip is entered into the patient file.

15. The method according to claim 11, wherein a plurality of fourth files corresponding to a plurality of medical products are cross-referenced so that it is possible to tell the number of products, actual implantation and pathologies for which the products are used.

16. The method according to claim 1, further comprising the step of automatically re-ordering the product corresponding to the fourth file for the client.

17. The method according to claim 1, further comprising the step of using an Intranet or Internet computer network to interrogate and to communicate with a remote data storage server of the supplier to order and to transmit the fourth file and to update the first product file.

18. The method according to claim 1, further comprising the step of sorting and analyzing the first, second, third, and fourth files to identify automatically or semi-automatically products after use with a patient or patients affected by a potential or existing problem linked to said medical product or to a type of patient.

19. A system for tracking medical products packaged and marked with a reference, said reference being stored in a first product file, said system for tracking at least one of the packaged medical products by a client for subsequent use thereof for a patient listed in a second patient file of said client, wherein the system comprises:
 means for automatic and remote detection of the reference of the at least one medical product when the product is shipped,
 means for storing said reference in a third client file,
 means for automatic detection of removal or entry of the at least one medical product from or into stock,
 means for insertion of the reference of the at least one medical product into the second patient file corresponding to a patient of the client in which the at least one medical product is or will be implanted,
 means for forming a fourth file comprising partial references coming from the second patient file and comprising the references of the implanted product that have been determined for tracking and expurgated data which includes a patient identifier but protects the medical confidentiality of the patient, and
 means for automatic or semi-automatic remote transmission of the fourth file to a supplier of the medical product.

20. A system for tracking medical products packaged and marked with a reference, said reference being stored in a first product file, wherein at least one of the packaged medical products is stored at a client facility for subsequent use thereof for a patient listed in a second patient file of said client, the system comprising a third client file containing references recognized automatically by radio frequency or optical recognition means of the at least one packaged medical product, and
 means for forming a fourth file comprising the reference of an implanted product and partial references coming from the second patient file, said fourth file having expurgated data which includes a patient identifier but protects the medical confidentiality of a corresponding patient, and
 means for transmitting the fourth file to a supplier of the at least one medical product.

21. The system according to claim 20, further comprising cards having respectively attached thereto corresponding RFID microchips each associated with a corresponding medical product, wherein said cards are loaded with information on the patient and on the date and on the type of operation carried out, said cards being respectively used for storing additional information on post-operative action, and said system comprises means to determine the number of medical products, actual implantation and pathologies for which the products are used.

22. A system for tracking medical products packaged and marked with a reference, said reference being stored in a first product file, said system for storing at least one of the medical products for subsequent use thereof for a patient listed in a second patient file, the system comprising:
 a bar code reader or a contactless microchip reader configured to automatically detect the at least one medical product,
 a computer configured to store references in a third client file, and to detect removal and/or entry of one or more medical products from or into stock,
 the computer configured to insert references of the at least one medical product into the second file corresponding to the patient of the client in which the medical product is or will be implanted,
 said computer configured to form a fourth file comprising the references of the implanted product and partial references coming from the second patient file and having expurgated data which includes a patient identifier but protects the medical confidentiality of the patient, and
 said computer configured to automatically or semi-automatically transmit the fourth file to a supplier of the at least one medical product.

23. The system according to claim 19, further comprising means for detecting products or the products' packaging by optical recognition.

24. The system according to claim 19, further comprising means for detecting the medical products or the products' packaging by radio-frequency recognition.

25. The system according to claim 24, wherein the packaging of each medical product comprises an at least partly transparent face and in that the marking comprises a label stuck to the inside of said transparent face.

26. The system according to claim 25, wherein the label is stuck in the right-hand corner of said transparent face.

27. The system according to claim 19, wherein each medical product comprises a detachable microchip card adapted to store the first product file and second patient files.

28. The system according to claim 19, further comprising means for re-ordering automatically a medical product corresponding to the fourth file.

29. The system according to claim 19, further comprising means for using an Intranet or Internet computer network to interrogate and communicate with a remote data storage server of a supplier to order and to transmit the fourth file and to update the first product file.

30. The system according to claim 19, further comprising means for sorting and analyzing one or more of the files to identify, and mark automatically or semi-automatically products or patients affected by a potential or existing problem linked to said products or to a type of patient.

31. The system according to claim 19, wherein the medical products are surgical implants.

32. The system according to claim 19, wherein the medical products are medications.

33. The system according to claim 19, wherein each medical product comprises a card attached to an RFID microchip contained in the product packaging wherein said card is free of any patient identifier and said RFID microchip being loaded only with information on said product contained in said packaging, partial information on the patient, date and type of operation carried out are stored in said microchip, said card being configured to store additional information on post operative action.

34. The system according to claim 33, wherein said RFID microchip has an individual serial number enabling automatic recovery of all data for any previous operation, either directly by reading a file contained in the microchip or by automatic calling up a corresponding patient file.

35. The system according to claim 34, wherein each card is equipped further with a detachable portion arranged to be inserted into a memory card reader.

36. The system according to claim 34, further comprising means for automatically creating the fourth partial file when information from the microchip is entered into the second patient file.

37. The system according to claim 36, further comprising means for cross-referencing fourth partial files of various products to determine the number of products, actual implantations and pathologies for which the products are used.

* * * * *